US012279947B2

(12) United States Patent
Gan et al.

(10) Patent No.: US 12,279,947 B2
(45) Date of Patent: Apr. 22, 2025

(54) OSSICULAR PROSTHESES FOR MIDDLE EAR RECONSTRUCTION

(71) Applicant: The Board of Regents of the University of Oklahoma, Norman, OK (US)

(72) Inventors: Rong Z. Gan, Oklahoma City, OK (US); Betty Tsai Do, Danville, CA (US); Marcus A. Brown, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 973 days.

(21) Appl. No.: 16/748,353

(22) Filed: Jan. 21, 2020

(65) Prior Publication Data

US 2020/0246135 A1    Aug. 6, 2020

Related U.S. Application Data

(60) Provisional application No. 62/801,793, filed on Feb. 6, 2019.

(51) Int. Cl.
| | |
|---|---|
| *A61F 2/18* | (2006.01) |
| *B33Y 70/00* | (2020.01) |
| *A61F 2/30* | (2006.01) |
| *A61L 27/38* | (2006.01) |

(52) U.S. Cl.
CPC ............. *A61F 2/18* (2013.01); *B33Y 70/00* (2014.12); *A61F 2002/183* (2013.01); *A61F 2002/30948* (2013.01); *A61F 2240/001* (2013.01); *A61L 27/3834* (2013.01)

(58) Field of Classification Search
CPC .............. A61F 2/18; A61F 2002/183; A61F 2002/30948; A61F 2240/001; A61F 2240/002; B33Y 70/00; B33Y 80/00; A61L 27/3834; A61L 27/16; A61L 27/18;
(Continued)

(56) References Cited

U.S. PATENT DOCUMENTS

| | | | |
|---|---|---|---|
| 2017/0195801 A1* | 7/2017 | Rucker | ............... H04R 25/606 |
| 2018/0042718 A1* | 2/2018 | Remenschneider | ......................... A61L 27/3839 |

(Continued)

OTHER PUBLICATIONS

Jackson, C.G., et al.; "Ossicular Chain Reconstruction: The Torp and Porp in Chronic Ear Disease"; Laryngoscope 93 (1983) 981-988.

(Continued)

*Primary Examiner* — Mohammad Ali
*Assistant Examiner* — Saad M Kabir
(74) *Attorney, Agent, or Firm* — Hall Estill Law Firm

(57) ABSTRACT

Ossicular prostheses, and methods for producing such, are disclosed for treatment of middle ear damage caused by a malady of the middle ear such as cholesteatoma. The ossicular prostheses comprises a strut component attached to a disc via a rigid or flexible connecting joint. The strut is attachable to a head or footplate of a subject's stapes. The disc is attachable to the subject's existing tympanic membrane, or, alternatively, to an artificial tympanic membrane graft. In some embodiments, a scaffold is used to support the ossicular prosthesis and the tympanic membrane graft.

18 Claims, 7 Drawing Sheets

(58) Field of Classification Search
CPC .... A61L 27/24; A61L 2300/414; A61L 27/54; A61L 2430/14
USPC .......................................................... 700/98
See application file for complete search history.

(56) References Cited

U.S. PATENT DOCUMENTS

2018/0116788 A1* 5/2018 Kozin ........................ A61F 2/18
2018/0311035 A1* 11/2018 Hirsch .................... A61B 34/10

OTHER PUBLICATIONS

Neumann, A., et al.; "Biomaterials for ossicular chain reconstruction. A review"; Biomaterials 34:12 (2003) 1052-0157.
Gan, R.Z., et al.; "Three-Dimensional Finite Element Modeling of Human Ear for Sound Transmission"; Annals of Biomedical Engineering 32:6 (2004) 847-859.
Chen, T., et al.; "Viscoelastic Properties of Human Tympanic Membrane"; Annals of Biomedical Engineering 35:2 (2007) 305-314.
Gan, R.Z., et al.; "Modeling of Sound Transmission from Ear Canal to Cochlea"; Annals of Biomedical Engineering 35:12 (2007) 2180-2195.
Cheng, T., et al.; "Mechanical properties of anterior malleolar ligament from experimental measurement and material modeling analysis"; Biomech Model Mechanobiol 7 (2008) 387-394.
Gehrking, E.; "Osteoplastic atticoantrotomy with autologous bone chips and a bony attic strut in cholesteatoma surgery"; Eur Arch Otorhinolaryngol 267 (2010) 1055-1066.
Gan, R.Z., et al.; "Mechanical properties of stapedial annular ligament"; Medical Engineering & Physics 33 (2011) 330-339.
Mantei, T., et al.; "Ossiculoplasty With Total Ossicular Replacement Prosthesis and Omega Connector: Early Clinical Results and Functional Measurements"; Otology & Neurology 32 (2011) 1102-1107.
Zhang, X., et al.; "Experimental measurement and modeling analysis on mechanical properties of incudostapedial joint"; Biomech Model Mechanobiol 10 (2011) 713-726.
Gan, R.Z., et al.; "Dynamic Properties of Round Window Membrane in Guinea ig Otitis Media Model Measured with Electromagnetic Stimulation"; Hear Res. 301 (2013) 125-136.
Landy, B.C., et al.; "Mechanical and in vitro investigation of a porous Peek foam for medical device implants"; J Appl Biomater Funct Mater 11:1 (2013) 35-44.
Meulemans, J., et al.; "Middle Ear Reconstruction Using the Titanium Kurz Variac Partial Osscular Replacement Prosthesis"; JAMA Otolaryngol Head Neck Surg. 139:10 (2013) 1017-1025.
Suzuki, H., et al.; "Partial Mastoid Obliteration Combined With Soft-wall Reconstruction for Middle Ear Cholesteatoma";123:8 (2014) 571-575.
Zhang, X., et al.; "Dynamic Properties of Human Stapedial Annular Ligament Measured With Frequency-Temperature Superposition"; Journal of Biomechanical Engineering 136 (2014) [081004] 1-7.

Mota, C., et al.; "Multiscale fabrication of biomimetic scaffolds for tympanic membrane tissue engineering"; Biofabricatoin 7 (2015) 025005; 22 pages.
Villar-Fernandez, M.A., et al.; "Outlook for tissue engineering of the tympanic membrane"; Audiology Research 5:117 (2015) 9-19.
Yokell, Z., et al.; "Dynamic Properties of Tympanic Membrane in a Chinchilla Otitis Media Model Measured With Acoustic Loading"; Journal of Biomechanical Engineering 137 (2015) [081006] 1-9.
Kozin, E.D., et al.; "Design, fabrication, and in vitro testing of novel three-dimensionally printed tympanic membrane grafts"; Hearing Research 340 (2016) 191-203.
Kuru, I., et al.; "A 3D-printed functioning anatomical human middle ear model"; Hearing Research 340 (2016) 204-213.
Wang, X., et al.; "3D finite element model of the chinchilla ear for characterizing middle ear functions"; Biomech Model Mechanobiol 15 (2016) 1263-1277.
Elicora, S.S., et al.; "The effects of surgery type and different ossiculoplasty materials on the hearing results in cholesteatoma surgery"; Eur Arch Otorhinolaryngol 274 (2017) 773-780.
Engebretson, B., et al.; "Tenocytic extract and mechanical stimulation in a tissue-engineered tendon construct increases cellular proliferation and ECM deposition"; Biotechnol. J. 12 (2017) [1600595] 1-10.
Engles, W.G., et al.; "Dynamic Properties of Human Tympanic Membrane After Exposure to Blast Waves"; Annals of Biomedical Engineering 45:10 (2017) 2383-2394.
Hirsch, J.D., et al.; "Surgical reconstruction of the ossicular chain with custom 3D printed ossicular prosthesis"; 3D Printing in Medicine 3:7 (2017) 1-8.
Hitt, B.M., et al.; "Dynamic property changes in stapedial annular ligament associated with acute otitis media in the chinchilla"; Medical Engineering and Physics 40 (2017) 65-74.
Kamrava, B., et al.; "Preliminary Model for the Design of a Custom Middle Ear Prosthesis"; Otology & Neurology 38 (2017) 839-845.
Mutlu, A., et al.; "A Comparison Study of Partial Ossicular Reconstruction Prosthesis (PORP) Placement under the Malleus or Tympanic Membrane Graft in the Presence of the Malleus"; J Int Adv Otol (2017) 4 pages.
Rusinek, R., et al.; "Dynamics of the middle ear ossicles with an SMA prosthesis"; International Journal of Mechanical Sciences 127 (2017) 163-175.
Stoppe, T., et al.; "Middle ear reconstruction with a flexible prosthesis"; Current Directions in Biomedical Engineering 3:2 (2017) 143-146.
Aron, M., et al.; "Auditory effects of autologous fat graft for TORP stabilization in the middle ear: a cadaveric study"; Journal of Otolaryngology—Head and Neck Surgery 47:17 (2018) 6 pages.
Gan, Rong Z., et al.; "An Animal Model of Cholesteatoma for Improvement of Middle Ear Surgical Reconstruction"; Biomedical Engineering Laboratory; 2018; 1 page.
Kong, J.S., et al.; "Comparative study of new autologous material, bone-cartilage composite graft, for ossiculoplasty with Polycel(R) and Titanium"; Clinical Otolaryngology 43 (2018) 434-439.

* cited by examiner

A

B

A

B

OSSICULAR PROSTHESES FOR MIDDLE EAR RECONSTRUCTION

CROSS-REFERENCE TO RELATED APPLICATIONS

The present patent application incorporates by reference the entire provisional patent application identified by U.S. Ser. No. 62/801,793, filed on Feb. 6, 2019, and claims priority thereto under 35 U.S.C. 119(e).

GOVERNMENT SUPPORT

This invention was supported by the National Institutes of Health under award number R01 DC011585. The government has certain rights in this invention.

BACKGROUND

Acquired cholesteatoma is a destructive condition of the middle ear resulting in erosion of the surrounding structures including the ossicles and bony wall by squamous tissue in the middle ear space, potentially causing severe hearing loss, vestibular dysfunction, facial paralysis, and/or intracranial complications. Surgical eradication of cholesteatoma is the primary treatment, but recurrence is common and hearing-related outcomes following surgery are uncertain.

Surgical reconstruction of the middle ear with tympanic membrane (TM) grafts and ossicular reconstruction prostheses, including partial ossicular reconstruction prostheses (PORPs) or total ossicular reconstruction prostheses (TORPs), is an important component in hearing restoration following surgical eradication of cholesteatoma. Although PORPs and TORPs have been used for middle ear reconstruction for decades, apart from material changes, there have been few alterations in the design of the prostheses. Chronic middle ear diseases like cholesteatoma and otitis media can alter middle ear mechanics, but there are no disease-specific or patient-specific prosthetic options available for use by surgeons. Current techniques for ossicular reconstruction rely on pre-manufactured prostheses that are selected and tailored at the time of surgery. Additionally, separate grafting material is often required to reconstruct the TM. However, the extent to which hearing is restored in individual patients who undergo middle ear reconstruction depends on the otologic surgeon's experience with diseased ears and the choice of prostheses. Consequently, there is a clinical demand for optimized, patient-specific prostheses that will reduce the recurrence of cholesteatoma and improve hearing-related outcomes. It is to this need that the present disclosure is directed.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure. Further, in the appended drawings, like or identical reference numerals may be used to identify common or similar elements, and not all such elements may be so numbered. The figures are not necessarily to scale, and certain features and certain views of the figures may be shown exaggerated in scale or in schematic in the interest of clarity and conciseness.

DETAILED DESCRIPTION

Figure 1:
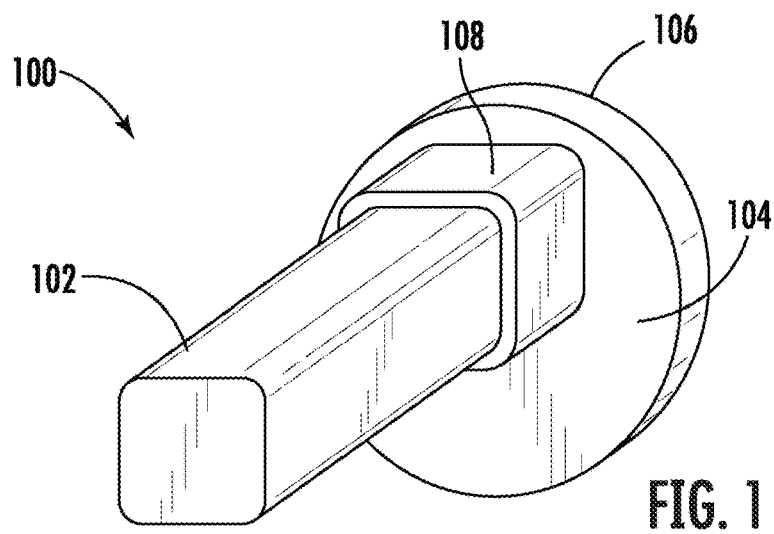
FIG. 1 is a perspective view of an ossicular prosthesis constructed in accordance with one embodiment of the present disclosure.

In at least certain non-limiting embodiments, the present disclosure is directed to an implantable, patient-specific, ossicular prosthesis (also referred to herein as a "prosthesis"), or an integrated tympanic membrane-ossicular prosthesis (hereinafter TM-ossicular prosthesis) for use in middle ear reconstruction. The ossicular prosthesis may be used to restore hearing following, for example, surgical eradication of cholesteatoma. In certain non-limiting embodiments, the prosthesis is comprised of a solid strut or a strut with a cavity (e.g., a "cap"), made of a rigid or flexible plastic or polymer (e.g., an acrylic), that attaches to a head or footplate of the patient's stapes. The strut is attached to a biodegradable disc or scaffold that attaches to the patient's tympanic membrane, or is attached to a a graft that serves as a new tympanic membrane.

In at least certain other non-limiting embodiments, the present disclosure is directed to methods of forming 3D-printed, patient-specific, TM-ossicular combination prostheses for use in middle ear reconstruction following (but not limited to) surgical eradication of cholesteatoma. Computed tomography (CT) scans of a patient's ears, including (but not limited to) the ear canal, tympanic membrane (TM), ossicles, and interior wall of the middle ear, can be used to create three-dimensional computer-aided design (CAD) models using readily available software. These models can then be used to identify structural damage within a given patient's ear or ears caused by (but not limited to) cholesteatoma. In at least certain non-limiting embodiments, the CAD model would then be replicated in a physical form using cadaveric temporal bone. A CT scan of the physical replica can then be performed in the same manner, creating a second 3D CAD model from which the patient-specific ossicular prosthesis or TM-ossicular prosthesis can be designed. This prosthesis can then be 3D-printed and tested for fit in the cadaveric replica. After final adjustments, the ossicular prosthesis or TM-ossicular prosthesis can then be surgically implanted in a patient's ear.

Before further describing various embodiments of the compositions and methods of the present disclosure in more detail by way of exemplary description, examples, and results, it is to be understood that the embodiments of the present disclosure are not limited in application to the details of methods and compositions as set forth in the following description. The embodiments of the compositions and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the composition, or the variation that exists among the objects, or study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The terms "about" or "approximately", where used herein when referring to a measurable value such as an amount, percentage, temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units therefore refers to and includes all values or ranges of values of the units, and fractions of the values of the units and integers within said range, including for example, but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of about 100 units to about 2000 units therefore can be used to set the lower and upper boundaries of a range in accordance with the embodiments of the present disclosure.

Figure 2:
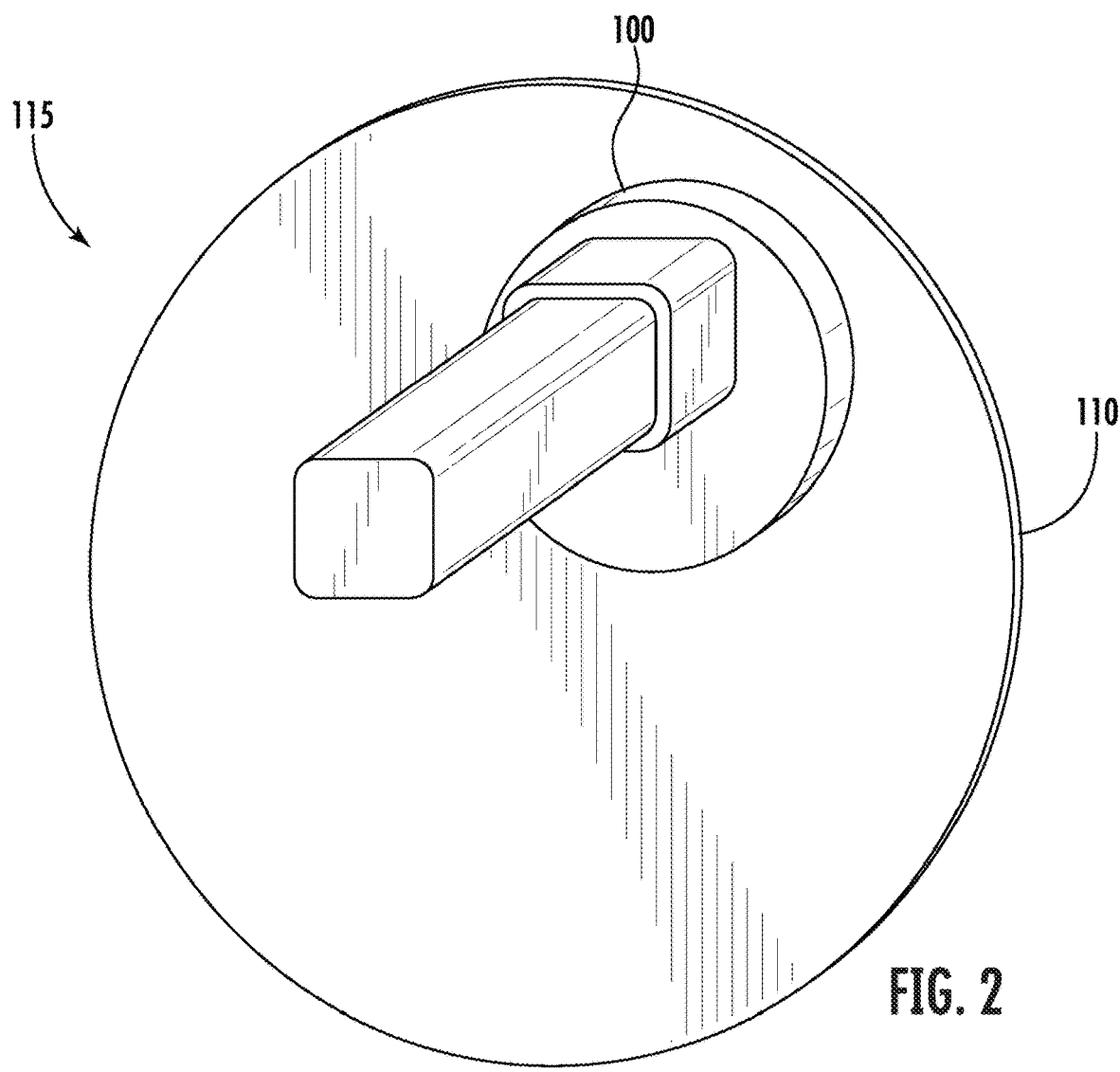
FIG. 2 is a perspective view of the ossicular prosthesis of FIG. 1 attached to a tympanic membrane (TM) or to a tympanic membrane graft to form an integrated TM-ossicular prosthesis.

Turning now to the drawings, FIG. 1 illustrates an ossicular prosthesis 100 constructed in accordance with the present disclosure. The ossicular prosthesis 100 includes an elongated strut 102 which is attached to a surface 104 of a disc 106 by a joint 108. The joint 108 may be constructed of a rigid or flexible material. In a non-limiting embodiment, the ossicular prosthesis 100 is constructed of a rigid acrylic material. The strut 102 is attachable to a footplate of a recipient patient's stapes (not shown) when, for example, the head of the stapes is eroded due to progression of cholesteatoma or other ossicle-damaging condition. The disc 106 is intended to attach to a surface of the recipient patient's own tympanic membrane (TM) or, in an embodiment such as shown in FIG. 2, to a tympanic membrane graft 110 forming an integrated TM-ossicular prosthesis 115 for use when the recipient patient's tympanic membrane has been excessively compromised or rendered irreparable due to the progression of cholesteatoma.

Figure 3:
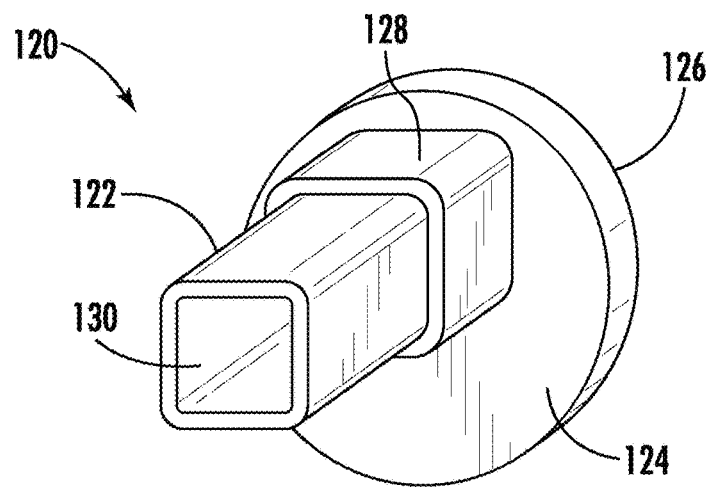
FIG. 3 is a perspective view of an alternate embodiment of an ossicular prosthesis constructed in accordance with of the present disclosure, constructed so as to fit over a portion of a patient's stapes.
Figure 4:
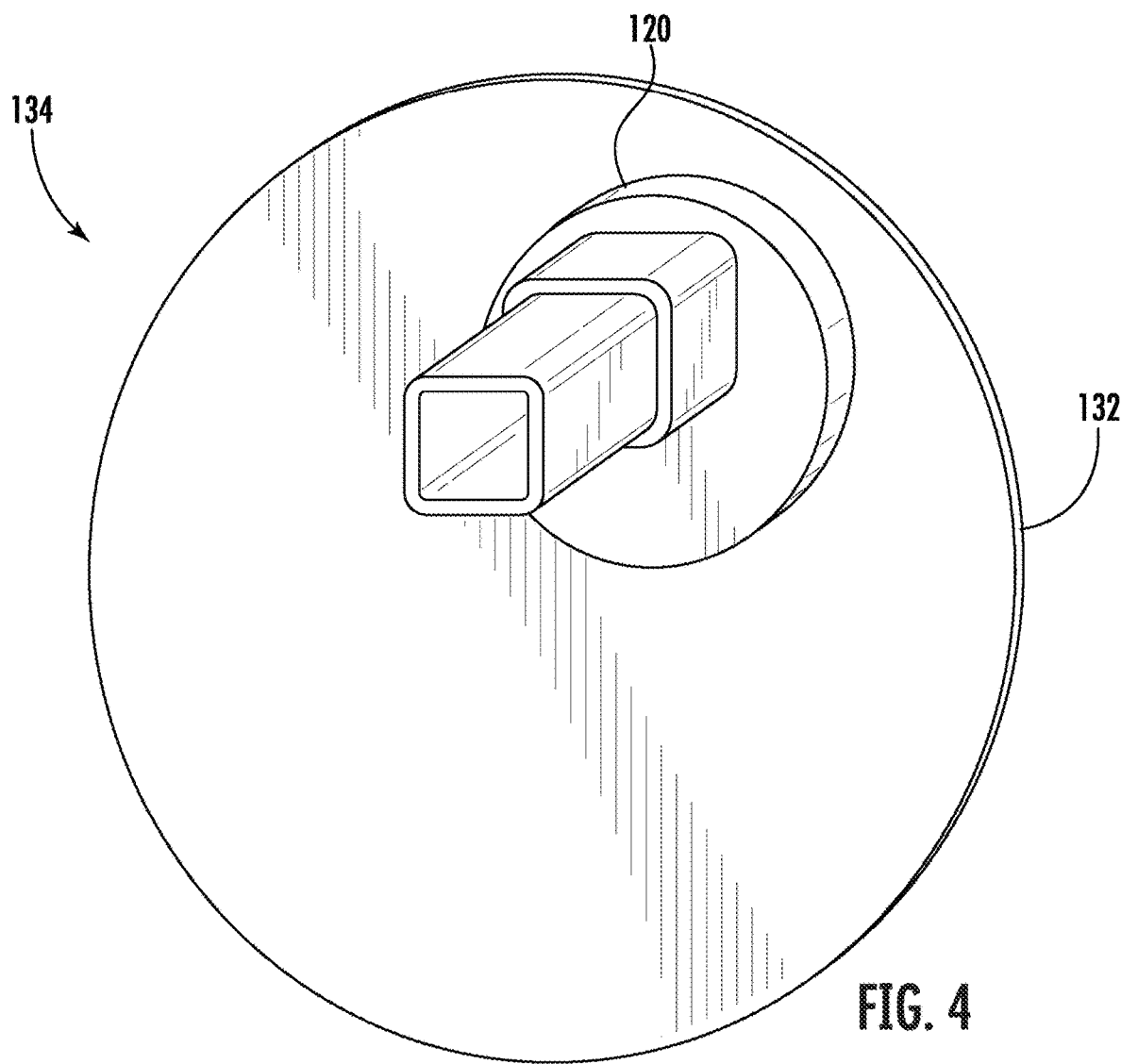
FIG. 4 is a perspective view of the ossicular prosthesis of FIG. 3 attached to a tympanic membrane (TM) or to a tympanic membrane graft to form an integrated TM-ossicular prosthesis.

In another non-limiting embodiment (FIGS. 3 and 4), the structure of the ossicular prosthesis is constructed to be compatible with a portion of an ossicle of the patient, for example a stapes that is completely or substantially intact. FIG. 3 illustrates an ossicular prosthesis 120 constructed in accordance with the present disclosure. The ossicular prosthesis 120 has a strut 122 attached to a surface 124 of a disc 126 by a joint 128. The strut 122 has a cavity 130 sized and configured to contain, in at least one non-limiting example, a portion of the completely or partially intact stapes of the patient. The disc 126 is intended to attach to the patient's tympanic membrane, or, in at least one non-limiting example, to a tympanic membrane graft 132 when the tympanic membrane has been compromised or rendered irreparable, forming an integrated TM-ossicular prosthesis 134 (FIG. 4). The fabrication process for this TM-ossicular prosthesis 134 would, in at least one non-limiting embodiment, be conducted in the same manner as previously described.

Figure 5:
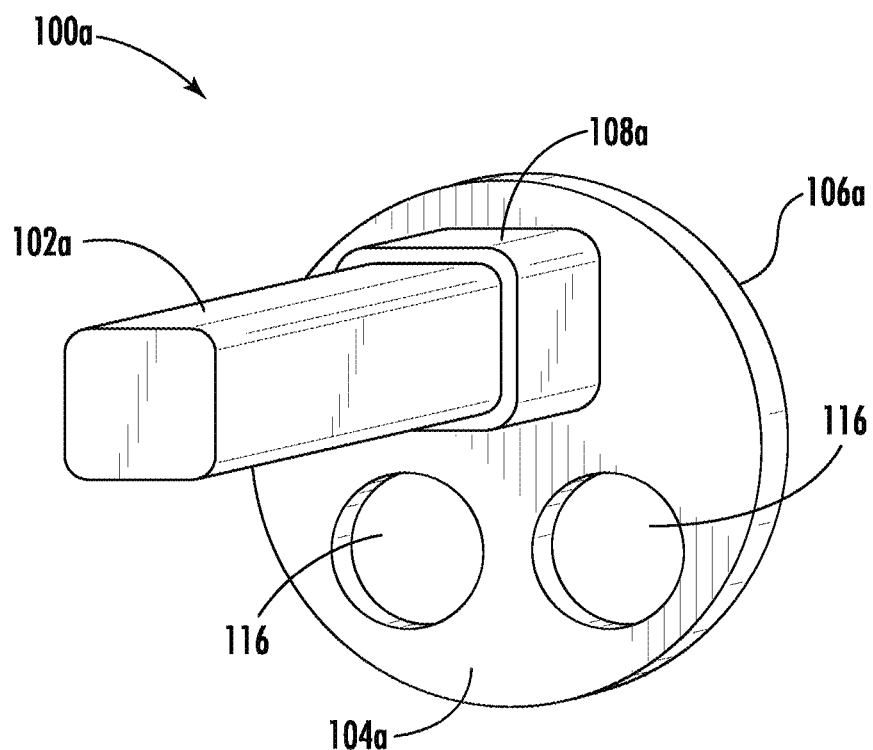
FIG. 5 is a perspective view of an ossicular prosthesis similar to the ossicular prosthesis of FIG. 1 but having a pair of holes in the disc portion.
Figure 6:
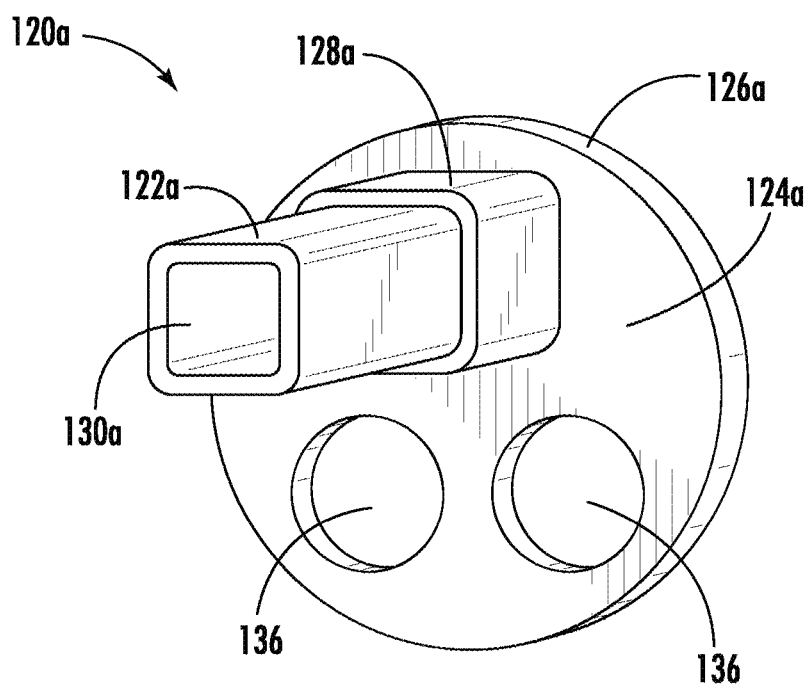
FIG. 6 is a perspective view of an ossicular prosthesis similar to the ossicular prosthesis of FIG. 3 but having a pair of holes in the disc portion.

In other non-limiting embodiments, the ossicular prostheses described above and elsewhere herein may be constructed to have one or more holes in the disc portion thereof to enable the surgeon to more easily manipulate the prosthesis during implantation. FIGS. 5 and 6 illustrate such modifications.

For example, as shown in FIG. 5, an ossicular prosthesis 100a includes an elongated strut 102a which is attached to a surface 104a of a disc 106a by a joint 108a. The disc 106a may comprise one or more holes 116. The embodiment of FIG. 5 has two holes 116. The joint 108a may be constructed of a rigid or flexible material. In a non-limiting embodiment, the ossicular prosthesis 100a is constructed of a rigid acrylic material. The strut 102a is attachable to a footplate of a recipient patient's stapes (not shown) when, for example, the head of the stapes is eroded due to progression of cholesteatoma or other ossicle-damaging condition. The disc 106a is intended to attach to a surface of the recipient patient's own tympanic membrane (TM) or, in an embodiment such as shown in FIG. 2, to a tympanic membrane graft forming an integrated TM-ossicular prosthesis (such as integrated TM-ossicular prosthesis 115 in FIG. 2) for use when the recipient patient's tympanic membrane has been excessively compromised or rendered irreparable due to the progression of cholesteatoma.

In another example, as shown in FIG. 6, an ossicular prosthesis 120a includes an elongated strut 122a which is attached to a surface 124a of a disc 126a by a joint 128a. The strut 122a has a cavity 130a sized and configured to contain, in at least one non-limiting example, a portion of the stapes of the patient. The disc 126a may comprise one or more holes 136. The embodiment of FIG. 6 has two holes 136. The disc 126a is intended to attach to the patient's tympanic membrane, or, in at least one non-limiting example, to a tympanic membrane graft 132a when the tympanic membrane has been compromised or rendered irreparable, forming an integrated TM-ossicular prosthesis 134a such as shown in FIG. 4. The joint 128a may be constructed of a rigid or flexible material. In a non-limiting embodiment, the ossicular prosthesis 120a is constructed of a rigid acrylic material. The disc 126a is intended to attach to a surface of the recipient patient's own tympanic membrane (TM) or, in an embodiment such as shown in FIG. 4, to a tympanic membrane graft forming an integrated TM-ossicular prosthesis (such as integrated TM-ossicular prosthesis 134 in FIG. 4) for use when the recipient patient's tympanic membrane has been excessively compromised or rendered irreparable due to the progression of cholesteatoma.

Figure 7A:
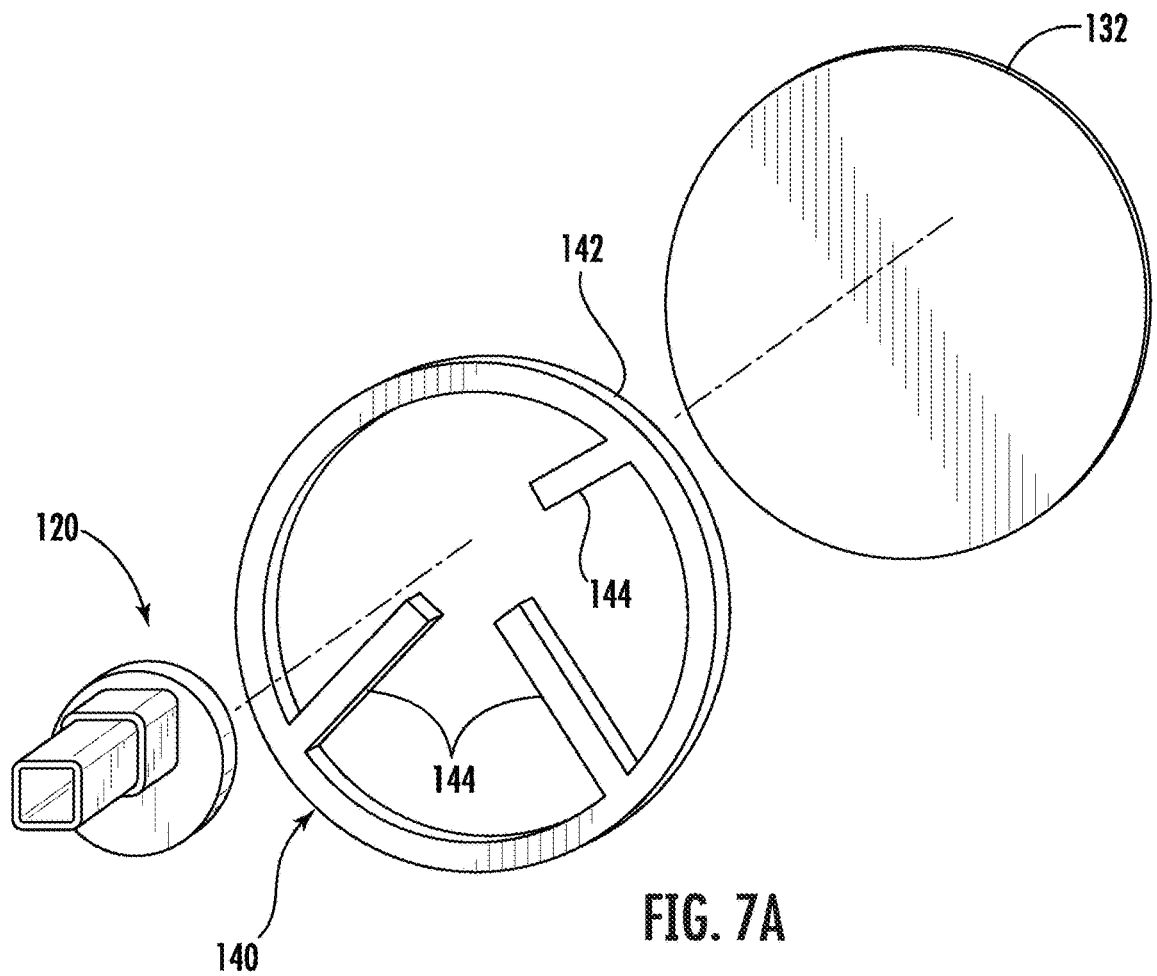
FIG. 7A is a perspective view of a scaffold with a plurality of ribs, to which an ossicular prosthesis and a tympanic membrane graft can be attached to form an assembly in accordance with one embodiment of the present disclosure.
Figure 7B:
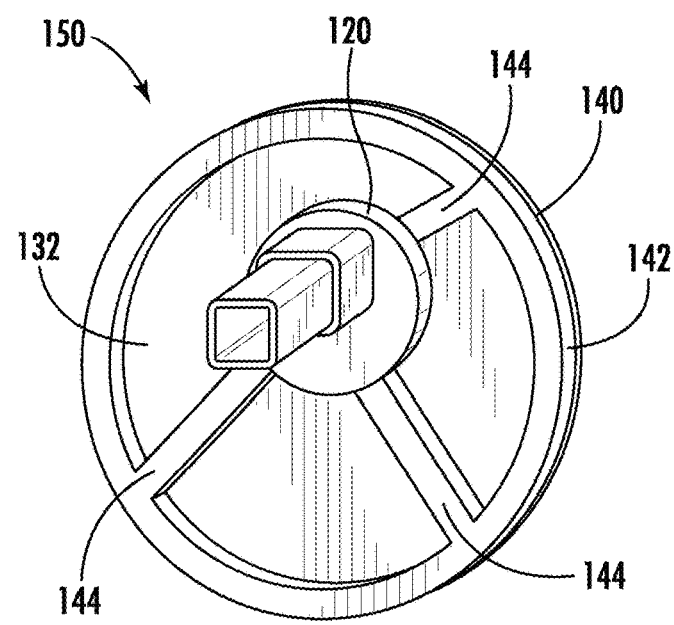
FIG. 7B is a perspective view of the components shown in FIG. 7A formed into an integrated TM-ossicular prosthesis-scaffold assembly.

In cases of severe cholesteatoma, wherein the patient's tympanic membrane has been compromised to the extent that there is no sufficient remnant upon which a TM graft can be affixed, the TM graft can be affixed to a TM-prosthesis scaffold structure 150 as exemplified in one non-limiting embodiment in FIGS. 7A and 7B. The TM-prosthesis scaffold structure 150 is constructed with a scaffold 140 having a rim 142 and a plurality of ribs 144 extending radially-inwardly from the rim 142. The TM graft 132 is attached to a back surface of the rim 142 and an ossicular prosthesis such as ossicular prosthesis 100, 100a, 120, or 120a (or any other ossicular prosthesis embodiment described or otherwise contemplated herein) is attached to and supported by the ribs 144. The scaffold 140 may be fabricated from a flexible polylactic acid material that is biodegradable and biocompatible. An exemplary 3D printer suited to such a purpose may be the Pro2 3D Printer by Raise3D, Inc. In at least some circumstances, the structures of the ear may be sufficiently compromised by damage resulting from, but not limited to, cholesteatoma to require additional support for the prosthesis prior to implantation. In a non-limiting embodiment, the 3D-printed tympanic membrane and/or the ossicular prosthesis may be affixed to the scaffold 140 with a biocompatible adhesive such as but not limited to a cyanoacrylate material, a fibrin glue, or Dermabond (TM). The scaffold 140 may be fabricated and incorporated with the other elements of the prosthesis in the manner previously described, and can be utilized with PORP-type prosthesis embodiments or TORP-type prosthesis embodiments. As described elsewhere herein, the scaffold 140 and/or tympanic membrane graft (e.g., 110 or 132) can be optionally seeded with mesenchymal stem cells (MSCs) which have been pre-cultured in a basal media after their isolation. The MSCs assist the TM-prosthesis scaffold structure 150 in adhering to and integrating with the surrounding bony tissue. The ossicular prosthesis 120 (partial or total) is printed on top of the scaffold 140 prior to seeding. In at least one non-limiting example, this is achieved by way of a two-step process wherein the scaffold 140 is printed first and then the scaffold 140 is placed onto the stage of another printing system to print the remaining components to form the of the TM-prosthesis scaffold structure 150.

Any of the joints which connect a strut to a disc (e.g., strut 102 and disc 106) may comprise a rigid joint or a flexible joint (e.g., constructed from a rubber-like material) depending on the particular conditions, physical shape, and other needs and charcteristics of the patient's middle ear. The pliability of the joint may mimic the flexibility of a healthy ossicular chain. This embodiment of the ossicular prosthesis may or may not include a tympanic membrane graft.

Figure 8:
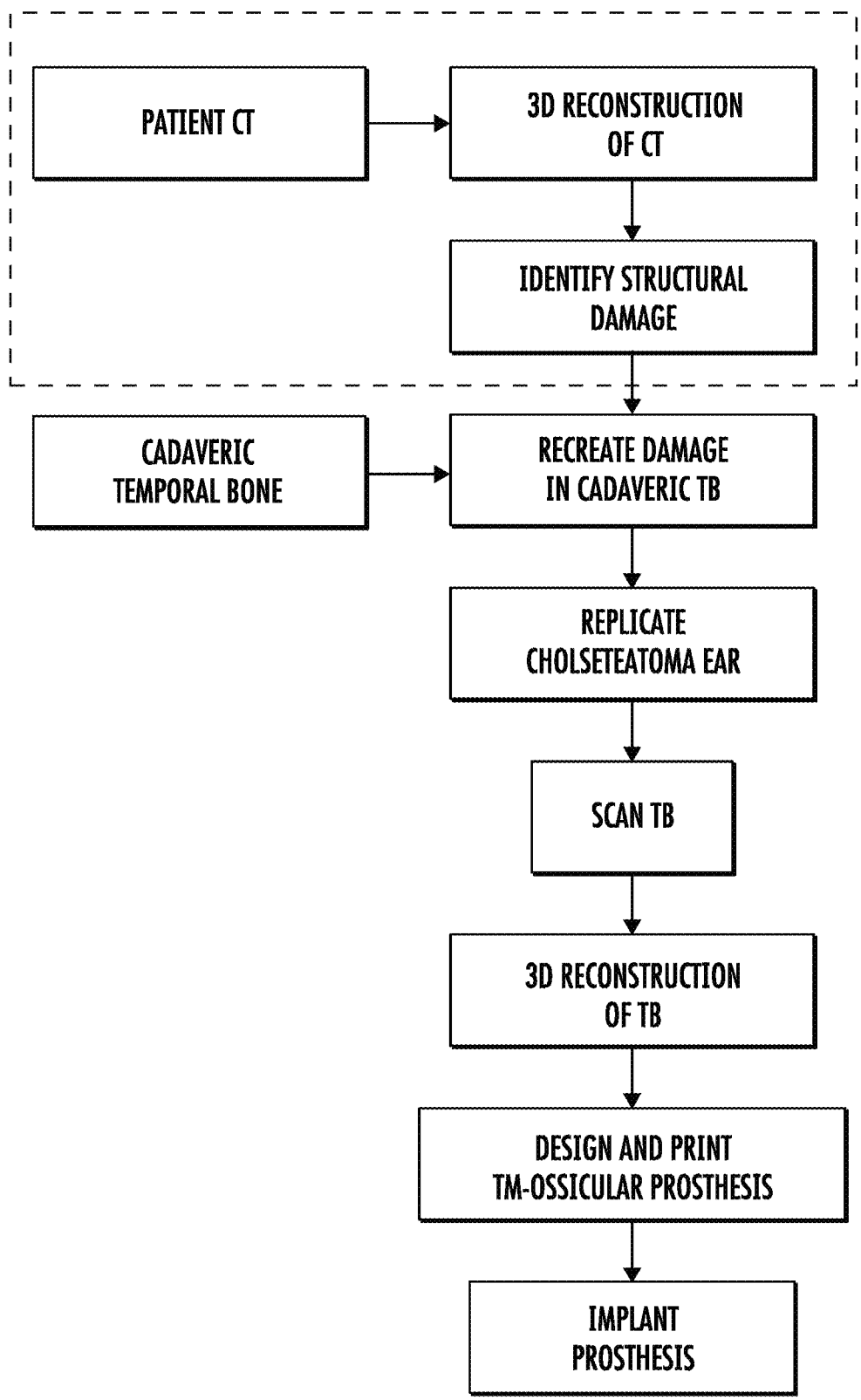
FIG. 8 is a flowchart showing a non-limiting embodiment of a method of forming an ossicular prosthesis as described in the present disclosure.
Figure 9:
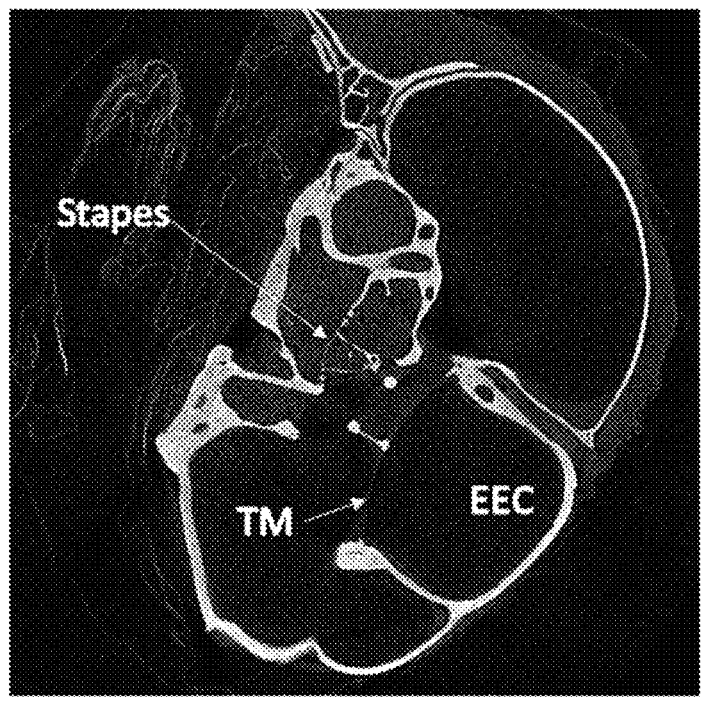
FIG. 9 shows (A) a micro computed tomography (CT) image of a cross-section through a normal bulla of a chinchilla ear, showing a stapes, tympanic membrane (TM) and EEC, and (B) a 3D model of a chinchilla bulla constructed from the CT image in A.
Figure 9:
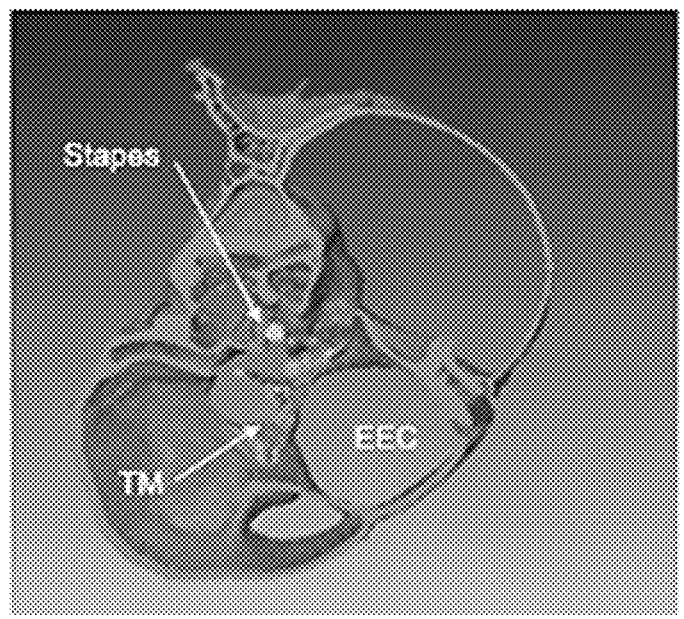
Figure 10:
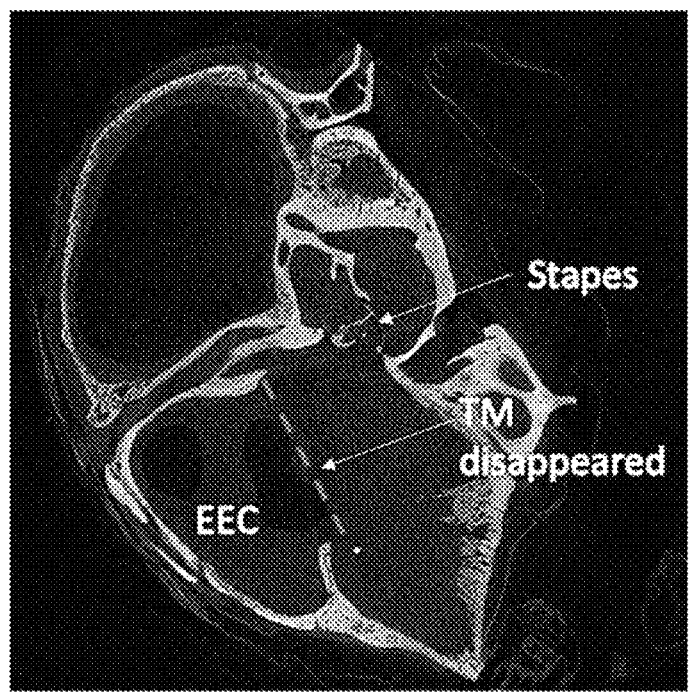
FIG. 10 shows (A) a micro CT image of a cross-section through a bulla of a chinchilla ear damaged by cholesteatoma, showing a stapes, position of the missing tympanic membrane and EEC, and (B) a 3D model of a chinchilla bulla constructed from the CT image in A.
Figure 10:
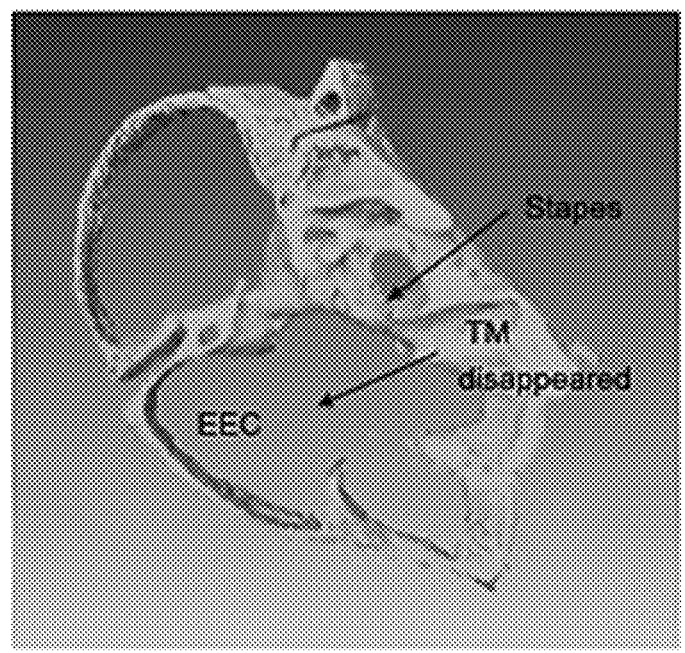

In a non-limiting embodiment of the present disclosure, as represented in FIG. 8, to construct a patient-specific ossicular prosthesis of the present disclosure, axial CT images are taken of a patient's ear or ears, including the ear canal, middle ear, and inner ear, at for example, a 0.625 mm resolution. The images are segmented using readily available software. An exemplary software suite suited to such a task is Amira™ by Visage Imaging, Inc. From these images the ear canal, tympanic membrane, ossicles, and interior wall of the middle ear cavity are identified and prepared for 3D modeling. An exemplary method for the identification of these structures and conversion to a 3D model is the SurfaceGen function in Amira. FIG. 9A-B for example shows a micro CT image of a cross-section through a normal bulla of a chinchilla ear, showing a stapes, tympanic membrane (TM) and external ear canal (EEC), and a 3D model of a chinchilla bulla constructed from the CT image. FIG. 10A-B for example shows a micro CT image of a cross-section through a bulla of a chinchilla ear damaged by cholesteatoma, showing a stapes, the position of the missing tympanic membrane and EEC, and a 3D model of a chinchilla bulla constructed from the micro CT image.

Once converted to a 3D model, portions of the middle ear which have been damaged, for example by cholesteatoma, can be identified, including for example the tympanic membrane, ear canal, and ossicles of the middle ear. In some embodiments, the structurally damaged portions of the ear can be replicated (recreated) as a physical model using bone, such as, but not limited to, fresh human temporal bone (TB). An exemplary material suited to such a purpose may be fresh human cadaveric TB provided by Science Care, Inc., based in Phoenix, Arizona In some embodiments, the replicated physical model of the damaged ear is recreated in the cadaveric TB using a drill and/or curette.

The physical model of the damaged ear is then scanned using a CT machine (e.g., at 0.625 mm resolution) and the CT images are converted to a 3D model in the same manner described above. The 3D model is then used to design the patient-specific ossicular prosthesis or integrated TM-ossicular prosthesis. The TM graft, when required, can be designed in the same manner, and will cover the patient's native tympanic membrane's area as well as any portions of the bony wall structures of the ear canal that are missing due to cholesteatoma or other maladies.

Once designed, the ossicular prosthesis (e.g., prosthesis 100 or 120) can then be 3D-printed (in acrylic for example), with the optional tympanic membrane component 110 to be printed in a manner described herein. The 3D-printed strut is specifically sized to engage the replica osscile (e.g., stapes) of the physical model. In some non-limiting embodiments, the constructed prosthesis is implanted into the replicated ear to evaluate how well it fits the replica ossicle and middle ear region and how it will be manipulated during surgery. Based on the evaluation, the design of the constructed prosthesis can be modified to improve fit and handling before finally being implanted in the patient. The middle ear transfer function (METF), i.e., TM movement in response to input sound pressure, can be measured using laser Doppler vibrometry (LDV) before replicating the TB.

In at least certain embodiments, as noted, the tympanic membrane graft 110 can be fabricated using a 3D printer in a manner readily apparent to those of ordinary skill in the art. An exemplary 3D printer well suited to such a purpose may be one developed by MakerBot Industries, LLC.

The artificial tympanic membrane graft devices, or simply "grafts," as described herein, may be acoustically tuned, i.e., adjusted, so the acoustic properties are adjusted for best sound conduction in a specific patient. The artificial tympanic membrane grafts, as noted elsewhere herein, may be attached to, or may comprise, or be constructed with, a scaffold. The scaffold may be constructed with ribs, with spaces In certain embodiments, an infill material may be used to fill the spaces between the ribs to create a solid, optionally semipermeable, artificial tympanic membrane graft. The ossicular prostheses described elsewhere herein can be attached to an artificial tympanic membrane graft, or to the ribs of a scaffold which comprises a TM graft material, or to which a TM graft is attached.

In some embodiments, the scaffold and/or (TM) grafts include agents that will induce cells from the patient's ear canal to migrate and colonize the graft within a time period of several weeks to months. In such embodiments, the TM grafts may be implanted without any living cells present. In other embodiments, the scaffold and/or (TM) grafts may comprise cells harvested from the subject, or from other subjects.

In some embodiments the TM graft and the scaffold can be manufactured by first "printing" the rim and ribs of the scaffold using a 3D printer that dispenses a first biocompatible (optionally biodegradable) material. The scaffold can be submerged in a curable liquid medium which fills the spaces between ribs of the scaffold, and then be cured to form a solid membrane between the ribs of the scaffold. Once cured, an ossicular prosthesis can be attached to the ribs of the TM graft, and the integrated prosthesis-TM graft can be implanted into the subject. In other embodiments the TM graft and scaffold can be manufactured by printing the scaffold and the space-filling material simultaneously or serially using a 3D printer that dispenses one or more types of biocompatible materials. The ribs and infill material may comprise two different printed materials, or in some circumstances may consist of different patterns of the same material. Once manufacture is complete, the graft is removed from the 3D printer's printing surface and may be cured by one or more methods, which may include for example, heat curing, curing by UV light, carbon dioxide or other gas, pressure, or cooling.

The scaffold rim and ribs may have any appropriate cross-sectional shape, including but not limited to circular, rectangular (e.g., square), triangular, or irregular. The diameter or thickness (at the widest point) of the rim and ribs may be on the order of tens to hundreds of micrometers. For example, the thickness of an individual rim or ribs may be from 5 to 50 µm, up to 500 to 800 µm, e.g., 10 to 100 µm, 100 to 500 µm, or 5 µm, 10 µm, 25 µm, 50 µm, 75 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, 500 µm, 550 µm, 600 µm, 650 µm, 700 µm, 750 µm, or 800 µm, or more or less as is technologically and physiologically appropriate. The scaffold may also be constructed to include the disc which connects the strut and connecting joint of the prosthesis to the ribs of the scaffold. In various embodiments, the scaffolds and/or TM grafts can have a diameter of 0.5 mm to 12 mm, e.g., 1, 2, 3, 5, 7, 9, 10, or 11 mm.

The scaffolds and TM grafts of the present disclosure can be created from any technologically appropriate material. For example, the material used may be selected to be biocompatible, capable of being manufactured to the size at which the scaffold and/or TM graft is designed, and possessing the necessary mechanical properties to facilitate the transmission of vibrations to the patient once implanted. Some examples of materials that can be used in the methods described herein include, but are not limited to, polydimethylsiloxane (PDMS) (which is non-absorbable by the body), hyaluronic acid (HA), poly(glycolic acid) (PGA), poly(lactic-co-glycolic acid) (PLGA), polylactic acid (PLA) (which is absorbable), poly(glycerol sebacate) (PGS), poly (N-isopropylacrylamide), poly(acrylic acid), poliglecaprone, polycaprolactone, poly(3-hydroxybuterate-co-3-hydroxyvalerate, pluronic PLA, polyurethane, polyvinyl alcohol (PVA), nylon, silk, silk fibroin, poliglecaprone, polycaprolactone (PCL) (which is absorbable by the body), polyester carbonate urethane urea (PECUU), poly octamethylene maleate anhydride citrate (POMaC), poly(octanediol-co-citrate) (POC), collagen, e.g., type III collagen, fibrin, collagen/fibrin mixture, elastin, chitosan, titanium dioxide, cellulose, gelatin, agarose, alginate, extracellular matrix, hydrogels, e.g., fibrin hydrogel, glucoseamino glycan hydrogels and sponges (e.g., Carbylan-GSX), cross-linked thiolated chondroitin sulfate, polylysine polymerized with latex, decellularized tissue (collagen and proteoglycans), fascia (temporal, lata, or muscle), fat, cartilage, perichondrium, and Gelfoam®. These materials can be used individually or in combinations of two of more different materials.

The scaffold and/or TM graft can be treated and/or functionalized to enhance adhesion of the component materials and to enhance cellular binding capabilities. For example, plasma treatment cleans the materials and also puts hydrophilic groups on the surfaces so that biologic materials, such as collagen and fibrin, can adhere more readily. Other treatment of scaffolds and TM grafts may include application of substances that improve cellular adhesion including oxidation, treatment with poly-D-lysine, 3-aminopropyl triethoxysilane (APTES), and cross-linking with glutaraldehyde (GA). In some embodiments, the scaffold and/or TM graft may comprise therapeutic drugs, such as antibiotics or anti-inflammatory agents. In some embodiments, the scaffold and/or TM graft may comprise growth factors such as epithelial growth factor (EGF), fibroblast growth factor (FGF), a vascular endothelial growth factor (VEGF), platelet-derived growth factor (PDGF), transforming growth factor (TGF), insulin-like growth factor (ILGF), interleukin-4, or other factors with similar biologic properties.

Additionally, the scaffold and/or TM graft can include, or be coated with in a separate step, cells or cellular materials. For example, cells can include, but are not limited to, one or more of fibroblasts, chondrocytes, keratinocytes, epithelial cells, and/or mesenchymal stem cells (e.g., derived from bone marrow, umbilical cord blood, or peripheral blood). These cells can be harvested from the patient who is to receive the implant or from a relative of the patient, or from a human subject unrelated to the patient who is to receive the implant, or from another mammalian species.

In other embodiments the ossicular prosthesis, scaffold, and/or TM graft may be constructed from or comprise materials disclosed in Published U.S. Patent Applications 2006/0024826, 2007/0162119, 2007/0082052, 2007/0038298, and 2016/0228606, each of which is incorporated by reference herein in its entirety.

As noted above, drugs, growth factors, cells, and/or cellular adhesion and invasion materials can be mixed with or added to the infill material or scaffold material or coated onto or soaked into the scaffold and/or infill material. However, in some implementations, some or all of these drugs, growth factors, and/or cellular adhesion and invasion materials can instead be applied to the exterior surfaces of the graft devices either before or after implantation.

In one non-limiting embodiment of a process for manufacturing a TM graft, the scaffold is printed with a 3D printer, and the scaffold is submerged in a liquid curable material after the scaffold is printed for filling in the spaces between the ribs of the scaffold. In a different process, the scaffold and the infill material are both printed by the same or two different 3D printers. In another process, a scaffold is created by casting a first material in a first mold, and the scaffold spaces between the ribs are filled by 3D printing, use of a curable liquid material, or using a second casting with a second material or combination of materials together with the scaffold in a second mold.

A computer is used to control the 3D printer and associated equipment. The computer can be a general-purpose computer such as a desktop or server computer. The computer includes software to create manufacturing instructions for other elements of the system. The 3D printer is a 3D printer capable of printing one or more scaffolds based on manufacturing instructions received from the computer. A curing oven and plasma treater may be used to cure the printed scaffold and/or applying a plasma treatment to the printed scaffold. A hot plate and infill station may be used to provide a temperature-controlled environment in which the scaffold can be infilled to form the TM graft. The TM graft may be incubated in a temperature-controlled environment. The computer can receive various parameters based on a CT scan and/or 3D model to direct the manufacture of the ossicular prostheses and/or TM graft.

The present disclosure is directed to at least the following non-limiting embodiments:

Clause 1. A method of producing a subject-specific ossicular prosthesis, comprising the steps of (1) obtaining a computed tomography (CT) scan of an ear region of the subject, the ear region comprising an ear canal and a middle ear region, the middle ear region comprising a tympanic membrane, ossicles, and a middle ear cavity interior wall; (2) using the CT scan of the ear region to formulate a first 3D middle ear model of the ear region; (3) replicating the first 3D middle ear model as a physical middle ear model; (4) obtaining a CT scan of the physical middle ear model; (5) using the CT scan of the physical middle ear model to formulate a second 3D middle ear model of said ear region; (6) using the second 3D middle ear model to identify damaged portions of the ear canal and/or middle ear region of the ear region and design a subject-specific ossicular prosthesis sized and configured to replace the damaged portions of the ear canal and/or middle ear region of the subject; (7) constructing the subject-specific ossicular prosthesis; and (8) implanting the constructed subject-specific ossicular prosthesis into the physical middle ear model to confirm that the constructed subject-specific ossicular prosthesis has a size and configuration which enables the subject-specific ossicular prosthesis to fit into the ear canal and/or middle ear of the subject.

Clause 2. The method of clause 1, wherein the designed subject-specific ossicular prosthesis further comprises a tympanic membrane portion.

Clause 3. The method of clause 1 and/or 2, wherein the tympanic membrane portion further comprises mesenchymal stem cells and/or at least one growth factor.

Clause 4. The method of any one of clauses 1-3, wherein the subject-specific ossicular prosthesis is constructed by 3D printing.

Clause 5. The method of any one of clauses 1-4, wherein the physical middle ear model is constructed of bone.

Clause 6. The method of clauses 5, wherein the bone is human temporal bone.

Clause 7. The method of any one of clauses 1-6, wherein the subject-specific ossicular prosthesis comprises a strut for connecting to a stapes of the subject.

Clause 8. The method of clause 7, wherein the strut is connectable to a footplate of the stapes, or comprises a cavity sized and configured to receive a portion of the stapes.

Clause 9. The method of clause 7, wherein the strut is connected to a disc via a connecting joint.

Clause 10. The method of clause 9, wherein the disc comprises at least one hole.

Clause 11. The method of any one of clauses 9 and/or 10, wherein the disc is connected to a tympanic membrane portion.

Clause 12. The method of any one of clauses 1-11, wherein the constructed subject-specific ossicular prosthesis is attached to a scaffold, wherein the scaffold is optionally biodegradable.

Clause 13. The method of clause 12, wherein the scaffold comprises a tympanic membrane portion.

Clause 14. The method of clause 12 or 13, wherein the scaffold comprises a rim and a plurality of ribs.

Clause 15. The method of any one of clauses 12-14, wherein the scaffold comprises mesenchymal stem cells and/or at least one growth factor.

Clause 16. The method of any one of clauses 1-16, further comprising implanting the constructed subject-specific ossicular prosthesis into the ear region of the subject.

Clause 17. An ossicular prosthesis specific to a subject, constructed using the method of any one of clauses 1-16.

Clause 18. The ossicular prosthesis of clause 17, comprising a tympanic membrane portion.

Clause 19. The ossicular prosthesis of clause 18, wherein the ossicular prosthesis and the tympanic membrane portion are attached to a scaffold.

Clause 20. The ossicular prosthesis of clause 19, wherein the tympanic membrane portion and/or the scaffold further comprise mesenchymal stem cells and/or at least one growth factor.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the various components and compositions described herein, the methods described herein or in the steps or the sequence of steps of the methods described herein without departing from the spirit and scope of the present disclosure.

What is claimed is:

1. A method of producing a subject-specific ossicular prosthesis, comprising:

obtaining a computed tomography (CT) scan of an ear region of the subject, the ear region comprising an ear canal and a middle ear region, the middle ear region comprising a tympanic membrane, ossicles, and a middle ear cavity interior wall;

using the CT scan of the ear region to formulate a first 3D middle ear model of the ear region;

replicating the first 3D middle ear model as a physical middle ear model;

obtaining a CT scan of the physical middle ear model;

using the CT scan of the physical middle ear model to formulate a second 3D middle ear model of said ear region;

using the second 3D middle ear model to identify structural damage in the ear region and design a subject-specific ossicular prosthesis;

constructing the subject-specific ossicular prosthesis to comprise a strut having a first end attached to a disc via an intervening joint and a second end comprising a cavity which is dimensioned to contain and be secured to a portion of a stapes ossicle of the subject's ear, wherein the disc is configured for attaching to a tympanic membrane of the subject; and implanting the constructed subject-specific ossicular prosthesis into the physical middle ear model to confirm that the constructed subject-specific ossicular prosthesis has a size and configuration which enables the constructed subject-specific ossicular prosthesis to fit within the middle ear of the subject.

2. The method of claim 1, wherein the subject-specific ossicular prosthesis is constructed by 3D printing.

3. The method of claim 1, wherein the physical middle ear model is constructed of bone.

4. The method of claim 3, wherein the bone is human temporal bone.

5. The method of claim 1, wherein the disc comprises at least one hole.

6. The method of claim 1, further comprising: implanting the constructed subject-specific ossicular prosthesis into the ear region of the subject.

7. A method of producing a subject-specific ossicular prosthesis, comprising:
   obtaining a computed tomography (CT) scan of an ear region of the subject, the ear region comprising an ear canal and a middle ear region;
   using the CT scan of the ear region of the subject to construct a first 3D model of the ear region;
   identifying structural damage in the middle ear region from the first 3D model;
   replicating the damage of the middle region as a physical middle ear model;
   obtaining a CT scan of the physical middle ear model;
   using the CT scan of the physical middle ear model to construct a second 3D middle ear model of said ear region recreating the structural damage in the middle ear region;
   designing a subject-specific ossicular prosthesis sized and configured to replace the damaged portions of the middle ear region; and
   constructing the subject-specific ossicular prosthesis to comprise a disc, a tympanic membrane (TM) graft, and a strut having a first end which is attached to a disc via an intervening joint and a second end comprising a cavity which is dimensioned to contain and be secured to a portion of a stapes ossicle of the subject's ear, wherein the disc is attached to the TM graft forming an integrated TM-ossicular prosthesis.

8. The method of claim 7, wherein the TM graft further comprises at least one of mesenchymal stem cells and a growth factor.

9. The method of claim 7, wherein the subject-specific ossicular prosthesis is constructed by 3D printing.

10. The method of claim 7, wherein the physical middle ear model is constructed of bone.

11. The method of claim 10, wherein the bone is human temporal bone.

12. The method of claim 7, further comprising:
   implanting the constructed subject-specific ossicular prosthesis into the physical middle ear model to confirm that the constructed subject-specific ossicular prosthesis has a size and configuration which enables the constructed subject-specific ossicular prosthesis to fit into the middle ear of the subject.

13. The method of claim 12, further comprising:
   implanting the constructed subject-specific ossicular prosthesis into the ear region of the subject.

14. The method of claim 1, wherein the subject-specific ossicular prosthesis consists of the strut, the disc, and the intervening joint.

15. The method of claim 1, wherein the structural damage is caused by cholesteatoma or another ossicle-damaging condition.

16. The method of claim 7, wherein the integrated TM-ossicular prosthesis consists of the strut, the disc, the intervening joint, and the TM graft.

17. The method of claim 7, wherein the structural damage is caused by cholesteatoma or another ossicle-damaging condition.

18. The method of claim 7, wherein the disc comprises at least one hole.

* * * * *